United States Patent [19]

Mura et al.

[11] Patent Number: 4,879,243
[45] Date of Patent: * Nov. 7, 1989

[54] USE OF SUBSTITUTED ORTHO-QUINONES AS ELECTRON TRANSFER AGENTS IN ANALYTICAL DETERMINATIONS

[75] Inventors: Albert J. Mura; Robert W. Zercie, both of Rochester, N.Y.

[73] Assignee: Eastman Kodak Company, Rochester, N.Y.

[*] Notice: The portion of the term of this patent subsequent to May 24, 2005 has been disclaimed.

[21] Appl. No.: 53,916

[22] Filed: May 26, 1987

[51] Int. Cl.$^4$ ............................................. G01N 33/48
[52] U.S. Cl. ........................................ 436/63; 436/84; 436/91; 436/93; 436/96; 436/128; 436/164; 436/904
[58] Field of Search ...................... 436/63, 84, 91, 93, 436/96, 128, 164, 904

[56] References Cited

U.S. PATENT DOCUMENTS 3,415,718 12/1968 Forkman et al. .
4,284,704 8/1981 Fleming et al. .
4,341,858 7/1982 Chaffee et al. .
4,525,453 6/1985 Guardino et al. ................... 436/904
4,746,007 5/1988 Mura et al. ........................... 436/93

FOREIGN PATENT DOCUMENTS 2740013 of 0000 Fed. Rep. of Germany .

OTHER PUBLICATIONS

Lin et al, J. Med. Chem., 17(5), pp. 558–561 (1974).
Lin et al. J. Med. Chem., 17(7), pp. 668–672 (1974).

Primary Examiner—Peter Chin
Attorney, Agent, or Firm—J. Jeffrey Hawley

[57] ABSTRACT

Certain methanol soluble ortho-benzo or -naphthoquinones are useful electron transfer agents. They are particularly useful in the detection of cells in urine.

7 Claims, No Drawings

USE OF SUBSTITUTED ORTHO-QUINONES AS ELECTRON TRANSFER AGENTS IN ANALYTICAL DETERMINATIONS

CROSS-REFERENCE TO RELATED APPLICATIONS

Reference is made to the following copending and commonly assigned applications: U.S. Ser. No. 699,374 Filed Feb. 7, 1985 by A. J. Mura et al entitled USE OF SUBSTITUTED QUINONE ELECTRON TRANSFER AGENTS IN ANALYTICAL DETERMINATIONS; U.S. Ser. No. 824,776 filed Jan. 31, 1986 by Belly et al entitled REDUCIBLE COMPOUNDS AND ANALYTICAL COMPOSITIONS, ELEMENTS AND METHODS UTILIZING SAME; U.S. Ser. No. 868,479 filed May 30, 1986 by Mura et al entitled LIGHT-STABLE REDUCIBLE COMPOUNDS AND ANALYTICAL COMPOSITIONS, ELEMENTS AND METHODS UTILIZING SAME; U.S. Ser. No. 890,051 filed July 28, 1986 by E. R. Schmittou entitled COBALT CONTAINING REAGENTS AND METHODS FOR THE DETERMINATION OF ANALYTES IN AQUEOUS FLUIDS; and U.S. Ser. No. 868,855 filed May 30, 1986 by mura et al entitled WATER-COMPATIBLE REDUCIBLE COMPOUNDS AND THEIR USE IN ANALYTICAL COMPOSITIONS AND METHODS.

FIELD OF THE INVENTION

This invention relates to clinical chemistry. In particular, it relates to analytical compositions, elements and methods which utilize certain substituted quinone electron transfer agents to determine analytes (e.g. living cells) in aqueous liquids (e.g. biological fluids).

BACKGROUND OF THE INVENTION

Chemical analysis of liquids, such as water, milk and biological fluids is often desirable or necessary for health maintenance and diagnostic treatment. Various compositions and elements to facilitate such analyses are known. Such compositions and elements generally include a reagent composition for determining a substance under analysis, termed an analyte herein. The analyte can be a biological organism or a chemical substance. This reagent composition, upon interaction with the analyte, provides a detectable change (e.g. dye formation).

Recently, much work has been directed to developing compositions and elements which are useful for rapid and highly quantitative diagnostic or clinical analysis of biological fluids such as whole blood, serum, plasma, urine and the like.

For the rapid and effective diagnosis and treatment of infectious diseases, it is desirable to be able to detect the bacteria causing the disease as rapidly as possible. Infections of the urinary tract are among the most common bacterial diseases, second in frequency only to infections of the respiratory tract. In fact, in many hospitals, urinary tract infections are the most common form of nosocomial infections, often following the use of catheters and various surgical procedures. Most urinary tract infections (UTI) result from ascending infection by microorganisms introduced through the urethra and vary in severity from an unsuspected infection to a condition of severe systemic disease. Such infections are usually associated with bacterial counts of 100,000 ($10^5$) or more organisms per mL of urine, a condition referred to as significant bacteriuria. Under normal conditions, urein is sterile, although contamination from the external genitalia may contribute up to 1,000 ($10^3$) organisms per mL in properly collected and transported specimens.

Significant bacteriuria may be present in a number of pathological conditions involving microbial invastion of any of the tissues of the urinary tract, or may result from simple bacterial multiplication in the urine without tissue invasion. The infection may involve a single stie such as the urethra, prostate, bladder, or kidney, although frequently it involves more than one site. Infection restricted to the urine may present itself as asymptomatic bacteriuria, i.e., a condition which manifests no overt signs or symptoms of infection. Early treatment of this condition can prevent the development of more serious conditions, e.g., pyelonephritis (inflammation of the kidney and the renal pelvis). The rapid detection of bacteria by a reliable method would therefore facilitate an early and specific diagnosis.

Further, in order to insure that a prescribed antiobiotic is in fact effective in treating an infection, repeated tests during therapy are required. The need for simple, rapid bacteriuria tests is thus clear. Moreover, in view of the frequent unsuspected asymptomatic occurrences of UTI among children, pregnant women, diabetics and geriatric populations, diagnosis of which may require collection and testing of several specimens, bacteriuria tests must be sufficiently simple and economical to permit routine performance. Again, this illustrates the need for a rapid and inexpensive bacteriuria detection method.

Determination of certain analytes, notably living cells (such as bacteria, yeast, etc.), is best accomplished using a reduible composition which provides a detectable species in the presence of an electron transfer agent (ETA). The electron transfer agent is first reduced by the living cell. The reduced ETA then reduces the reducible composition to generate a detectable species which is then detected. Phenazine methosulfate (PMS) is a typical ETA.

Unfortunately, PMS and structurally related ETAs are unstable in aqueous solutions. In the related application mentioned above relating to ETAs (U.S. Ser. No. 699,374), there is disclosed an improved class of ETA compounds. These compounds are substituted benzoquinones or naphthoquinones. The ETAs of that invention provide many advantages over the previously known ETAs. However, still further improvements were sought. More particularly, the specific ETAs in the examples of that application have less than the desired sensitivity. Improved sensitivity was particularly sought with the reagents described in the copending applications described above.

SUMMARY OF THE INVENTION

The present invention provides a means for the determination of analytes, e.g. microorganisms, with improved sensitivity compared to known assays.

Therefore, in accordance with this invention, a composition for determination of an analyte in a liquid comprises:

(a) an electron transfer agent (ETA) which is a stable methanol soluble, 1,2-benzoquinone with methoxy groups or a fused 1,4-dioxane ring in positions 4 and 5 or with a substituted or unsubstituted lower alkoxy group at position 4 and a fused five- or six- membered carbocyclic or hetercyclic ring at positions 5 and 6, (b) a reducible composition which provides a detectable species when reduced by the ETA.

Further, this invention provides a method for the determination of an analyte in a liquid. This method comprises the steps of:

A. at a pH of 9 or less, contacting a sample of the liquid with described quinone electron transfer agent (ETA), and a reducible composition which provides a detectable species upon reduction by the ETA, and B. detecting the detectable species.

DETAILED DESCRIPTION OF THE INVENTION

As noted above, the advantages obtained with the present invention are achieved due to the use of particular electron transfer agents (ETAs) in the practice of this invention. These ETAs are highly compatible with both aqueous and oleophilic environments. They have sufficient hydrophilic character to be soluble in aqueous buffer solutions. At the same time, they have sufficient oleophilic character to allow interaction with electron donors within the cells.

The ortho-quinones useful in the present invention are structurally similar to the quinones described in the related ETA application described above (U.S. Ser. No. 699,374). Unexpectedly however, the present quinones give improved response compared to the examples in that application as is seen in the comparative examples which are included herein.

It is preferred that the ETAs useful in the practice of this invention have a reduction potential ($E_{\frac{1}{2}}$) within the range of from about $-320$ to about $+400$ mV when measured in an aqueous buffer solution at pH 7 so that the compounds can act as electron transfer agents with cells. Preferably, the $E_{\frac{1}{2}}$ of the ETA is in the range of from about $-185$ to about $+400$ mV. The desired $E_{\frac{1}{2}}$ is achieved by having the appropriate substituents on the quinone nucleus of the compound. With the teaching provided herein, a person skilled in synthetic chemistry would know which substituents to put on the quinone nucleus to obtain the desired $E_{\frac{1}{2}}$. Reduction potential measurements can be made according to conventional electrochemical techniques using either differential pulse polarography or cyclic voltametry (see, e.g. Sawyer and Roberst, Jr., *Experimental Electrochemistry for Chemists*, John Wiley & Sons, New York, 1974).

Representative ETAs useful in this invention are illustrated below:

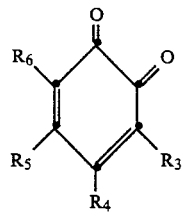

wherein $R_4$ and $R_5$ are methoxy and $R_3$ and $R_6$ are independently selected from the group consisting of hydrogen, substituted or unsubstituted lower alkoxy, such as methoxy or ethoxy or substituted or unsubstituted lower alkyl, such as methyl or ethyl, or $R_4$ and $R_5$, taken together, form a fused 1,4-dioxane ring and $R_3$ and $R_6$ are as defined above, or $R_5$ and $R_6$, taken together, form a fused five- or six- membered carbocyclic or heterocyclic ring such as phenyl, furyl, pyridyl, thienyl or 1,4-dioxy, $R_4$ is a substituted or unsubstituted lower alkoxy, such as methoxy, ethoxy or methoxycarbonylmethoxy and $R_3$ is as defined above.

The ortho-quinones should be stable. By stable we mean that the compound can be sythesized, isolated and kept at about 37° C. at least during the assay, i.e., for at least several hours.

Representative ortho-quinones useful in the practice of the present invention include:

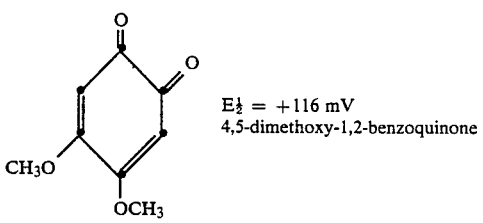

Cpd A.   $E_{\frac{1}{2}} = +116$ mV
4,5-dimethoxy-1,2-benzoquinone

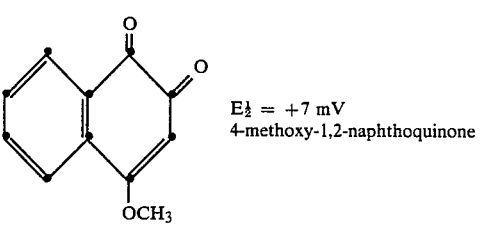

Cpd B.   $E_{\frac{1}{2}} = +7$ mV
4-methoxy-1,2-naphthoquinone

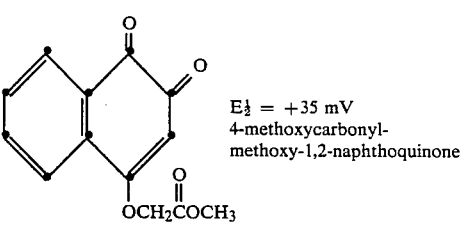

Cpd C.   $E_{\frac{1}{2}} = +35$ mV
4-methoxycarbonyl-methoxy-1,2-naphthoquinone

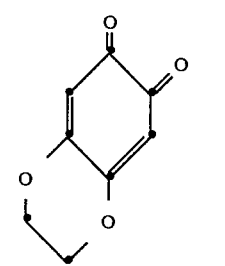

Cpd D.

1,4-Benzodioxane-6,7-dione

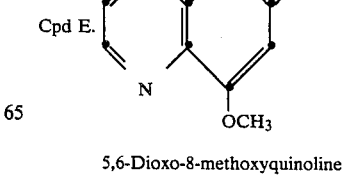

Cpd E.

5,6-Dioxo-8-methoxyquinoline

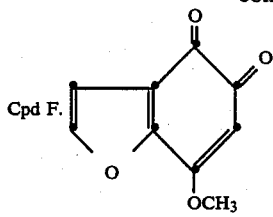

Cpd F.

4,5-Dioxo-7-methoxybenzofuran

As noted, the ortho-quinones useful in the present invention should be methanol soluble. By methanol soluble it is meant that a solution of the compound that is at least about 0.005M can be formed in methanol. Predissolving the ortho-quinone in a small amount of methanol facilitates forming an aqueous solution. Other solvents, such as N,N-dimethylformamide are also useful for predissolving the ortho-quinone. Compounds soluble in methanol will also be soluble in these solvents.

Reduction potentials (measured as the half-wave potentials $E_{\frac{1}{2}}$) were determined using a polarographic analyser. The solution medium was sodium phosphate buffer (pH 7.0, ionic strength=0.1). Measurements were made against a standard calomel electrode. Values are reported versus the normal hydrogen electrode.

The ETAs described herein can be prepared using starting materials and procedures known in the art. For example, reference is made to A. Takuwa et al, *Bull. Chem. Soc. Japan*, 59, 2959 (1986) and Y. Itoh et al, *Bull. Chem. Soc. Japan*, 52, 2169 (1979).

The ETAs described herein are used in combination with a reducible composition which can provide a detectable species when reduced by the ETA. The detectable species can be obtained by the reducible compound undergoing a change to become detectable. Alternatively, the detectable species can be obtained by release from the reducible composition. The detectable species can be a material which is directly detectable by a suitable means, as well as a material which can react with other substances, e.g. other analytes, enzymes, mordants, metal ions or other materials to provide a detectable species. Such species includes those detectable by radiometric means, including chromogens (e.g. dyes or pigments) which can be detected colorimetrically, and fluorogens (e.g. fluorescent dyes or probes) which can be detected fluorometrically. Additionally, the detectable species can be a phosphorescent species, a radioactively tagged species, or a chemiluminescent species, or any other detectable species knonw to one skilled in the art.

Useful reducible materials include tetrazolium salts which can be reduced to form colorimetric dyes, dichloroindophenol dyes which can be reduced to colorless compounds, and other dyeproviding materials which can be reduced.

Examples of useful classes of chromogens are azo, azomethine, nitrophenol, indophenol, indoaniline and triarylmethane dyes, and others known in the art, with azo dyes being preferred. Examples of useful classes of fluorogens are coumarin, fluorescein and rhodamine fluorescent dyes, and others known in the art.

Particularly useful moieties are chromogens and fluorogens having a first spectral absorption band prior to release and a second spectral absorption band when measured after release. Useful compositions of this type are described in U.S. Ser. No. 824,776 filed Jan. 31, 1986 by Belly et al entitled REDUCIBLE COMPOUNDS AND ANALYTICAL COMPOSITIONS, ELEMENTS AND METHODS UTILIZING SAME; U.S. Ser. No. 868,479 filed May 30, 1986 by Mura et al entitled LIGHT-STABLE REDUCIBLE COMPOUNDS AND ANALYTICAL COMPOSITIONS, ELEMENTS AND METHODS UTILIZING SAME, and U.S. Ser. No. 868,855 filed May 30, 1986 by Mura et al entitled WATER-COMPATIBLE REDUCIBLE COMPOUNDS AND THEIR USE IN ANALYTICAL COMPOSITIONS AND METHODS, all cited above. These applications generally describe reducible intramolecular nucleophilic displacement compounds, referred to as "RIND" compounds. These compounds are of the general structure CAR-$(R)_n$ where n is 1 or 2, CAR- is a substituted or unsubstituted aromatic or quinone nucleus and R is a moiety which is comprises a shiftible detectable species. In preferred embodiments, the compounds are water compatible and light stable.

Particularly preferred reagents are the cobalt (III) containing reagents described in copending commonly assigned U.S. patent application Ser. No. 890,051 referenced above. In this application there is disclosed a reducible composition for the determination of reductants which comprises a water soluble cobalt(III) complex and a water soluble metallizable dye. The optional electron transfer agent which can be included in the composition can be the ortho-quinone electron transfer agents as described.

Another preferred reducible composition or redox reagent is described in copending commonly assigned U.S. patent application No. 718,301 filed 1 Apr. 1986 and entitled ANALYTICAL COMPOSITIONS, ELEMENTS AND METHODS UTILIZING REDUCTION OF FERRIC ION CHELATES TO FORM DETECTABLE DYES. In this application there is disclosed a composition which comprises a chelate of ferric ions and a ferric coordinating ligand which produces ferrous ions when reduced and a second ferrous ion coordinating ligand which preferentially coordinates ferrous ions to form a colored complex.

Many other redox reagents are known such as the compositions containing NAD, an electron carrier and a tetrazolium salt described in U.S. Pat. No. 4,351,899; the compositions containing a polyvalent metal ion chelate, and indicator capable of reacting with the metal ion and a buffering agent described in U.S. Pat. No. 4,303,409; and compositions containing a variety of reducable compounds such as described in U.S. Pat. Nos.: 3,331,752; 3,711,252; 4,101,381; 4,116,774; 4,224,034; and 3,954,412.

As noted the presently preferred reducible composition or redox reagent are cobalt(III) complex containing reagents. Cobalt(III) is a trivalent metal that typically has a coordination number of six. An extremely wide variety of ligands are known to coordinate to cobalt(III). If the ligands are selected so that the contaning a negative charge, a valence can be satisfied by the ligand. Conversely, if the ligand is electrically neutral, the valence must be satisfied by a non-coordinated counter-ion and a salt is formed. For use in the present invention, water soluble complexes are required. The cobalt(III) complex salts, being more water soluble are preferred.

Useful neutral ligands for forming Co(III) complexes include: ammonia, aliphatic amines, such as ethylenediamine, propylenediamine, diethylenetriamine; substituted or unsubstituted aromatic amines, such as aniline, 2-aminoethylaniline, 2,2'-bisaniline; substituted or unsubstituted heterocyclic amines, such as pyridine, 2,2'-bipyridine, 2-(aminomethyl)pyridine, 4,4'-dimethyl2,2'-bipyridine, 2,2',2''-terpyridine, morpholine, pyrimidine, pyridazine, 2,2'-bipyrazine, quinoline, isoquinoline, acridine, thiazole, imidazole, triazine, 1,10-phenanthroline, 5-nitrophenanthroline, 2,2'-bipyrimidine, 2,2'-diimidazole; and oxygen donor ligans, e.g. amides such as N,N-dimethylformamide and water. Any anion can be used as the counter ion. For convenience, halide ions are preferred such as chloride, bromide and iodide. Other useful counter anions include, for example, azide, thiocyanate, tetrafluoroborate, nitrate, perchlorate, hexafluorophosphate, sulfate, carbonate, sulfonate and carboxylate ions.

Anionic ligands may also coordinate with cobalt(III) provided the charge on cobalt(III) is not completely neutralized by the ligands, so that the complex is a salt and therefore water soluble. Useful anionic ligands include halide, i.e., chloride, bromide, iodide or fluoride, azide, thiocyanate, nitrite, carbonate, carboxylate, sulfonate, oxalate and 2,4-pentanedionate ions.

The presently preferred cobalt complex is [Co(ethylene diamine)$_2$(2,2'bipyridine)]Cl$_3$.

The other component that is used in the cobalt(III) containing reducible composition or redox reagent useful in the present invention is a water soluble metallizable dye. A very wide variety of dyes that are capable of coordinating with a cobalt(II) and (III) ion are useful. The dyes must be water soluble. Many of the specific dyes listed in the references below are not water soluble but can be easily made so by the incorporation of a suitable solubilizing group in the dye molecule by conventional methods. Conventional solubilizing groups such as carboxylic acid, sulfonic acid and sulfate groups are useful.

Preferred dyes are also tridentate ligands for cobalt. Tridentate ligands form more stable complexes and therefore can more easily displace ligands from the cobalt(II) complex.

With these criteria in mind, useful dyes and dye classes are disclosed in U.S. Pat. Nos. 4,396,546; 4,273,708; 4,272,434; 4,024,993; 4,147,544 and 4,419,435.

The preferred dyes are: 2-[(3-methyl-2-pyridyl)azo]-1-naphthol-4-sulfonic acid, monoammonium salt; 2-[(5-carboxy-2-pyridyl)azo]-1-naphthol-4-sulfonic acid, diammonium salt; and 2-[(3-methyl-5-sulfo-2-pyridyl)azo]-1-naphthol-4-sulfonic acid, diammonium salt.

The ETA and reducible composition can be combined with a buffer solution. Useful buffers include those which will maintain the pH of the composition at 9 or less, and preferably from about 6.5 to about 8. Representative buffers include phosphates, borates, N-2-hydroxy-ethylpiperazine-N'-2-ethane sulfonic acid, and others known in the art, e.g. those described by Bood et al in *Biochem.*, 5, p. 467 (1966) and *Anal. Biochem.*, 104, 300 (1980).

The compositions of this invention are useful for analytical determination (i.e. quantitative, semi-quantitative or qualitative detection) of aqueous or non aqueous liquids, e.g. biological fluids, manufacturing processes, wastewater, food stuffs, etc. Determinations can be made of various analytes, including living cells (e.g. bacteria, yeast, fungi, etc.), enzymes (e.g. lipase, glucose oxidase, lactate oxidase, creatine kinase, α-glycerophosphate oxidase, lactate dehydrogenase, alanine aminotransferase, aspartate aminotransferase and other NADH-based or peroxidase-based assays which include dehydrogenase or reductase enzymes), biological or chemical reductants other than living cells which will reduce the ETA (e.g. ascorbate, cysteine, glutathione, etc.), metabolizable substances (e.g. glucose, lactic acid, triglycerides, cholesterol, etc.), immunoreactants (e.g. antigens, haptens, etc.), and other determinations made via a single reaction or sequence of reactions which brings about reduction of the reducible compound and release of a detectable species.

The compositions of this invention are particularly useful in detecting or quantifying living cells in biological samples. Although any biological sample suspected of having living cells therein (e.g. food, tissue, ground water, cooling water, pharmaceutical products, sewage, etc.) can be analyzed for bacteria, yeast, fungi, etc. by this invention, the invention is particularly useful for bacterial detection in aqueous liquids, such as human and animal fluids (e.g. urine, cerebral spinal fluid, blood and the like as well as stool secretions) and suspensions of human or animal tissue. The practice of this invention is particularly important for detection of urinary tract infections in urine (diluted or undiluted).

The detection of living cells, and particularly of bacterial cells, is often carried out in the presence of a nutrient for those cells although its presence is not essential. Any nutrient media can be used which contains useful carbon, and optionally nitrogen, sources. Conventional nutrient mediums having proper components and pH are well known in the art. Particularly useful nutrients are readily metabolizable carbon sources, such as simple sugars (glucose, sucrose, raffinose, maltose, lactose, galactose, fructose, etc.), glycols (e.g. glycerol, sorbitol, etc.), carboxylic acids (e.g. acetic acid, lactic acid, citric acid, etc. or salts thereof) starch, tryptose and the like. Particularly useful nutrients are glucose or tryptose, alone or in combination.

The present invention is adaptable to either solution or dry element assays. For solution assay, an analytical composition containing a reducible composition (e.g. cobalt (III) containing reagents) which will provide a detectable species and an ETA can be prepared and mixed with a liquid test sample containing the living cells or analyte to be determined. The ETA can also be present in the test sample prior to mixing with the reducible composition. Generally the analytical composition is mixed with the test sample in a suitable container (e.g. test tube, petrie dish, beaker, cuvette, etc.). The resulting solution (or dispersion) is gently mixed and incubated for a relatively short time (i.e. up to about 30 minutes) at a temperature up to about 40° C., and generally from about 20° to about 40° C. The test sample is then evaluated by measuring the detectable species (e.g. chromogen or fluorogen) that has been released by reduction of the reducible composition. Such an evaluation can be done with suitable detection equipment.

In a preferred mode of practicing the present invention, the urine sample to be tested is filtered in an apparatus similar to that disclosed in U.S. Ser. No. 019,819 filed Feb. 27, 1987 by Hinckley entitled DISPOSABLE CONTAINER CONFIGURED TO PRODUCE UNIFORM SIGNAL. The reducible composition is then added and the presence of a color change is determined. Where it is desired to determine the type of infection that might be present, two urine samples can be tested. One untreated sample is tested to determine the presence or absence of cells of any type. A second sample is first treated with an anionic surfactant as is described is commonly assigned U.S. Pat. No. 4,525,435 issued 25 June 1985.

The solution assay can also be carried out by contacting a porous, absorbent material, e.g. paper strip, containing the test sample with the analytical composition. The analyte in the test sample can migrate from the porous material into the composition thereby initiating the analytical reactions needed for the determination.

Test strips can be used as a convenient way to carry measured amounts of analytical composition to the test solution. The test strip is placed into a solution that might already contain the cells to be determined. The reagents dissolve from the test strip into the solution so as to form the reaction solution. In preferred embodiments of the test strips of the present invention, the reagents are carried in a water soluble binder. When the test strip is immersed into the solution, the binder dissolves releasing the reagents. For reasons not understood, this mode of delivery of cobalt(III) containing reagents provides improved sensitivity in comparison to the use of freshly made solutions of the reagents. Useful water soluble polymers include N-vinylpyrrolidone polymers such as poly(N-vinyl-2-pyrrolidone) homopolymer as well as copolymers, e.g. copolymers with acrylamide such as poly(acrylamide-co-N-vinyl-2-pyrrolidone) 90:10 by weight.

Generally, in a solution assay, the amount of reducible compound in the reducible composition present is from about 0.001 to about 10 and preferably from about 0.05 to about 1, millimolar. The ETA is generally present in an amount of from about 0.001 to about 2 and preferably from about 0.05 to about 1, millimolar. Other reagents can be present in amounts readily determined by one skilled in the art.

Alternatively, this invention can be practiced in a "dry" assay which utilizes a dry analytical element. Such an element can be a simple absorbent carrier material, i.e. a thin sheet or strip of self-supporting absorbent or bibulous material, such as filter paper or strips, which contains the reducible composition and ETA or a dried residue of same. Such elements are known in the art as test strips, diagnostic elements, dip sticks, diagnostic agents and the like.

In one embodiment of this invention, an element for detection of microorganisms (e.g. yeast fungi, bacteria, etc.) in an aqueous liquid comprises an absorbent spreading zone containing an ETA and cobalt (III) containing reagents, both of which are described above. It is desirable that these elements also contain a nutrient for the living cells and a buffer which amintains physiological pH under conditions of use (i.e. when contacted with a 1–100 μl sample of liquid). Such an element can be used to detect bacteria, for example, in a urine sample (pretreated to eliminate reductive interferents) by physically contacting the sample and element in a suitable manner, and detecting the dye that results from the cobalt (III) reagents.

In a preferred embodiment in solution, there is provided a method for the determination of cells in a sample, said method comprising the steps of:

(1) separating the cells from the sample,
(2) washing the separated cells with:
 (a) an iron chelate solution and
 (b) a non-ionic surfactant solution
(3) contacting the washed cells with a reducible composition so as to produce a detectable change in the presence of the cells.

A wide variety of iron chelates are useful in this preferred embodiment. The chelate can be made by simply mixing an iron salt with a suitable ligand, many of which are known. Useful iron chelates include chelates of:

(a) Ethylenedinitrilotetraacetic acid
(b) Nitrilotriacetic acid
(c) Diethylenetriaminepentaacetic acid
(d) 1,3-Diamino-2-hydroxypropane-N,N,N',N'-tetraacetic acid
(e) 1,2-Diaminopropane-N,N,N',N'-tetraacetica cid
(f) Ethylenediamine-N,N'-diacetic acid
(g) Iminodiacetic acid
(h) N-Methyliminodiacetic acid
(i) trans-1,2-Diaminocyclohexane-N,N,N',N'-tetraacetic acid
(j) 1,3-Diaminopropane-N,N,N',N'-tetraacetic acid The currently preferred chelates are a, b, g and h.

In addition to the iron chelate, the cells are also washed with a solution of non-ionic surfactant. The iron chelate and the surfactant can be in the same solution or in separate solutions. Where the cells are separated from the sample by filtration, the iron chelate and the surfactant can be in the filter material in which case the wash solution is made in situ.

Useful non-ionic surfactants include octylphenoxypolyethoxy ethanols commercially available from Rohm and Haas Company under the Triton trade name (e.g. X-100, 102, 165 and 305); o-ninylphenoxypolyethoxy ethanosl commercially available from Olin Mathieson Co.; polyethyleneglycol ethers of alcohols available from Union Carbide Co. under the trade name Tergitol (e.g. 15-S-7 and 15-S-9); polyoxyethylene compounds commercially available from ICI Americas under the trade name Tween (e.g. 20, 80); and natural non-ionic surfactants such as deoxycholate. Currently preferred nonionic surfactants are Triton X-100, Triton X-405, Tween 20 and Tween 80.

In Example 1 below, the compoudn 4,5-dimethoxy-1,2-benzoquinone was used. This is compound "A" above. This compound was made by the method of Y. Itoh et al, *Bull. Chem. Soc. Japan,* 52, 2169 (1979) as follows:

A mixture of sodium iodate (20 g, 0.1 mol) and catechol (5.5 g, 0.05 mole) in dry methanol (500 mL) was heated to 60° C. for 20 hours. The mixture was cooled to room temperature and filtered and the filtrate was concentrated to ~50 mL. The remaining solution was cooled and the resulting crystals were collected by filtration and air dried. The solid was dissolved in methylene chloride and filtered and the resulting solid obtained from filtrate evaporation was recrystallized from isopropyl alcohol. The crystals were dissolved in a mixture of ethyl acetate and acetonitrile and passed through a plug of silica gel. Solvent removal yield 2.75 g (33%) of the desired product mp. 227°–228°. Other ortho-quinones used in the examples were made in a similar manner.

EXAMPLE 1

This example compares the detection of $1 \times 10^5$ Escherichia coli per mL with the ETA, 2,3-dimethoxy-5-methyl-1,4-benzoquinone, a para-quinone ETA disclosed in U.S. Ser. No. 699,374 described above and 4,5-dimethoxy-1,2-benzoquinone, an ortho-quinone ETA as presently described.

The following solutions were prepared (distilled tap water was used throughout):

A. Phosphate buffer: By mixing the appropriate amounts of solution X and Y below and diluting to a total volume of 500 mL a 0.05 M phosphate buffer of the required pH was prepared:

X: 0.1 M monobasic poatssium phosphate,
Y: 0.1 M dibasic potassium phosphate,
pH 6.80; 112.5 mL X and 137.5 mL Y,
pH 7.50; 40 mL X and 210 mL Y,
pH 7.80; 21.25 mL X and 228.75 mL Y.

B. Cell suspension: *Escherichia coli* cells (American Type Culture Collection No. 25922( were grown in brain heart infusion medium (Difco Labs) at 37° C. withotu shaking. Forty millilitres of cells that were grown overnight were harvested by centrifugation to form a pellet of cells. The pellet was resuspended in 25 mL of 0.05 M phosphate buffer (pH 7.5) and the resulting suspension was recentrifuged. The washed pellet was suspended in 25 mL of buffer, and an aliquot was diluted with the same buffer to obtain an absorbance of 0.833 at 620 nm, measured against a buffer blank. An absorbance of 0.833 has been determined to correspond to a cell concentration of $5 \times 10^8$ cells/mL. This solution was then diluted 1 to 100 to yield a $5 \times 10^6$ *E. coli*/mL stock suspension.

C. Glucose solution: 10% by weight glucose in filtered distilled water.

D. Cobalt solution: 41.44 mg of [Co(ethylene diamine)$_2$(2,2'-bipyridine)]Cl$_3$ was dissolved in 10 mL of 0.05 M, pH 7.80 phosphate buffer.

E. Dye solution: 30.5 mg of 2-[(5-carboxy-2-pyridyl)azo]-1-naphthol-4-sulfonic acid, diammonium salt was dissolved in 10 mL of 0.05 M, pH 7.80 phsphate buffer.

F. Electron transfer agent (ETA) solution: 0.01 M 2,3-dimethoxy-5-methyl-1,4-benzoquinone in methanol. (Comparative para-quinone ETA)

G. Electron transfer agent solution: 0.008 M 4,5-dimethoxy-1,2-benzoquinone in methanol. (an ortho-quinone ETA useful according to the invention)

The assay protocol utilized a mixture of 2.34 mL, pH 6.8 phosphate buffer, 25 μl stock solution C, 50 μl stock solution E, 500 μl stock solution D, 25 μl of either ETA solution F or G and finally 60 μl suspension B$_5$. The final concentration of *E. coli* was $1 \times 10^5$ cells/mL. The mixture was shaken and thermally equilibriated at 37° C. The reactions were followed over 30 min by monitoring the appearance of dye at 610 nm using a spectrophotometer. A background control was also run which contained all of the same components except the E. coli cells. The results are given in Table 1 as the difference in optical density (ΔOD after 30 minutes) minus background.

TABLE 1

| | Δ Optical Density at 30 min |
|---|---|
| ortho-quinone | 0.350 |
| para-quinone (comparative) | 0.075 |

The results clearly show the superiority of the ortho-quinone in comparison to the para-quinone.

EXAMPLES 2 AND 3

Example 1 was repeated except that the final cell concentratin was $1 \times 10^6$ cells/mL, the dye solution contained 35.7 mg of 2-[(3-methyl-5-sulfo-2-pyridyl)azo]-1-naphthol-4-sulfonic acid, diammonium salt dissolved in 10 mL of 0.05 M, pH 7.80 phosphate buffer and two different ETA's were used according to the invention. The ETA's were:

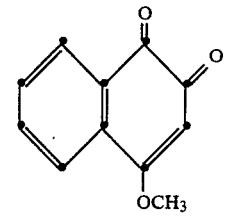

B and

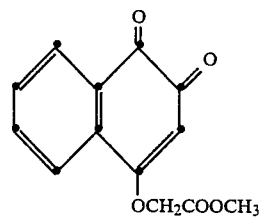

C

The ΔOD was determined for each as in example 1 as follows:

TABLE 2

| | | Δ OD |
|---|---|---|
| ortho-quinone B | 30 min. | 1.725 |
| ortho-quinone C | 18 min. | 1.077 |

EXAMPLE 4

This example compares the detection of *Escherichia coli* cells with the ETA, trimethyl-1,4-benzoquinone, a para-quinone ETA disclosed in U.S. Ser. No. 699,374 described above and 4,5-dimethoxy-1,2-benzoquinone, an ortho-quinone ETA as presently described. Instead of cobalt reagents, a RIND compound was used.

The following solutions were prepared (distilled tap water was used throughout):

A. Buffer: HEPES buffer ([N-2-hydroxethylpiperazine-N'-2-ethanesulfonic acid]), 0.05M, pH 7.8, filtered through a 0.2μ filter.

B. RIND compound: A solution containing a RINd compound of U.S. Ser. No. 868,855 was preapred. RIND compound V on page 16 of that application was dissolved in 250 μL of N,N-dimethylformamide (DMF). The DMF had been acidified with 0.1% sulfuric acid. This RIND solution was added to 25 mL of the HEPES buffer to form the RIND dispersion. The RIND compound had the structure:

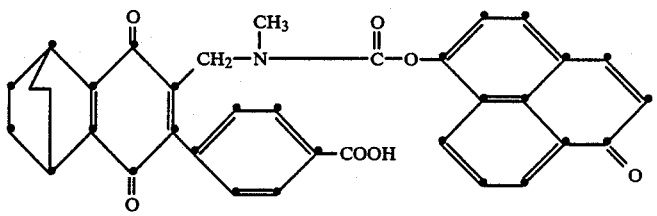

C. Glucose solution: Same as Example 1.

D. Cell Suspension: Same as Example 1. (5×10⁸ cells/mL stock solution)

E. Electron transfer agent solution: Same as Example 1 solution F. This is a comparative ETA referenced above.

F. Electron transfer agent solution: Same as Example 1 solution G except that the concentration was 0.01M. This is an ETA useful in the invention.

A reagent solution was prepared by mixing 500 μL of each of the glucose solution C, the RIND dispersion B and one of the two ETA solutions E or F. To the two reagent solutions that resulted were added 1380 μL of the HEPES buffer adn 120 μL of the cell suspension so that the final concentration of cells was 2×10⁷ cells/mL. Background controls were prepared which contained all of the components except the cells. optical densities were measured at 540 nm and the change in the optical density after 30 minutes, corrected for background was determined (ΔOD). The results are listed below in Table 3:

TABLE 3

|  | Δ Optical Density at 30 min |
|---|---|
| ortho-quinone | 0.800 |
| para-quinone (comparative) | 0.646 |

The results clearly show the superiority of the ortho-quinone in comparison to the para-quinone when using the RIND compound.

EXAMPLE 5

This example compares the detection of 1×10⁶ $E.\ coli$ per mL with 2,3-dimethoxy-5-methyl-1,4-benzoquinone, a para-quinone disclosed in U.S. Ser. No. 699,374 and thus a comparative compound; 4,5-dimethoxy-1,2-benzoquinone a preferred benzoquinone of the present invention; and 4,5-diethoxy-1,2-benzoquinone the next adjacent homolog of the dimethoxy compound. The diethoxy compound is not within the scope of the invention. The example was run in a manner similar to Example 1.

The data shown in Table 4 is the difference in optical density after 30 minutes, minus the background, for the three compounds tested. In the case of the dimethoxy compound of the invention, the difference in the optical density is after only 18 minutes. At this point the dye was depleted. For the other compounds, the data is for 30 min.

TABLE 4

| ETA | Δ OD |
|---|---|
| para-quinone (comparative) | 1.144 (30 min) |
| dimethoxy ortho-quinone | 1.314 (18 min) |
| diethoxy ortho-quinone (comparative) | 0.496 (30 min) |

The data indicate that the compound of the invention is superior to the para-quinone. A next adjacent homolog of a preferred compound of the invention is also inferior.

The invention has been described in detail with particular reference to preferred embodiments thereof, but it will be understood that variations and modifications can be effected within the spirit and scope of the invention.

What is claimed is:

1. A method for the determination of an analyte in a liquid comprising the steps of:
   A. at a pH of 9 or less contacting a sample of the liquid with a composition comprising
      (a) an electron transfer agent (ETA) which is a stable, ethanol soluble 1,2-benzoquinone with methoxy groups or a fused 1,4-dioxane ring in positions 4 and 5 or with a substituted or unsubstituted lower alkoxy group at position 4 and a fused five- or six-membered carbocyclic or heterocyclic ring at positions 5 and 6, said substituents being present such that the reduction potential, $E_{\frac{1}{2}}$, of said ETA falls within the range of about −320 to 400 mV,
      (b) a reducible composition which provides a detectable species when reduced by the ETA, and
   B. detecting said detectable species.

2. A method according to claim 1 wherein said liquid is urine and said analyte is cells.

3. A method according to claim 1 wherein said quinone has the structural formula:

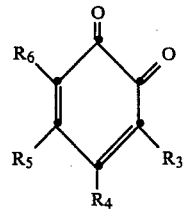

wherein $R_4$ and $R_5$ are methoxy and $R_3$ and $R_6$ are independently selected from the group consisting of hydrogen, substituted or unsubstituted lower alkoxy or substituted or unsubstituted lower alkyl, or $R_4$ and $R_5$, taken together, form a fused, 1,4-dioxane ring and $R_3$ and $R_6$ are as defined above, or $R_5$ and $R_6$, taken together, form a fused five- or six-membered carbocyclic or heterocyclic ring, $R_4$ is a substituted or unsubstituted lower alkoxy and $R_3$ is as defined above.

4. A method according to claim 1 wherein said quinone is selected from the group consisting of 4,5-dimethoxy-1,2-benzoquinone; 4-methoxy-1,2-naphthoquinone and 4-methoxycarbonylmethoxy-2,2-naphthoquinone.

5. A method according to claim 1 wherein said reducible composition comprises a water soluble cobalt(III) complex and a water soluble metalizable dye.

6. A method according to claim 1 further comprising a carbon source.

7. A method according to claim 1 wherein said composition comprises:
(1) 4,5-dimethoxy-1,2-benzoquinone
(2) [Co(ethylenediamine)$_2$(2,2'-bipyridine)]Cl$_3$
(3) 2-[(5-carboxy-2-pyridyl)azo]-1-naphthol-4-sulfonic acid diammonium salt.

* * * * *